United States Patent [19]
Nitshke

[11] 4,232,669
[45] Nov. 11, 1980

[54] PROTECTIVE SHEATH FOR SYRINGE NEEDLE

[75] Inventor: Norman L. Nitshke, Central Square, N.Y.

[73] Assignee: Bristol Myers Co., New York, N.Y.

[21] Appl. No.: 12,416

[22] Filed: Feb. 15, 1979

[51] Int. Cl.³ .............................................. A61M 5/00
[52] U.S. Cl. ................................ 128/218 N; 128/221
[58] Field of Search ................. 128/215, 216, 218 R, 128/218 S, 218 M, 218 N, 220, 221, 272

[56] References Cited

U.S. PATENT DOCUMENTS

| | | | |
|---|---|---|---|
| D. 238,617 | 1/1976 | Richman | D24/4 |
| 791,802 | 6/1905 | DeLisle | 128/218 N |
| 2,854,975 | 10/1958 | Cohen | 128/218 N |
| 2,857,912 | 10/1958 | Feinstone et al. | 128/215 |
| 3,376,866 | 4/1968 | Ogle | 128/220 |
| 3,434,473 | 3/1969 | Smith | 128/221 |
| 3,542,023 | 11/1970 | Ogle | 128/218 M |
| 3,677,245 | 7/1972 | Welch | 128/218 S |
| 3,678,931 | 7/1972 | Cohen | 128/220 |
| 3,826,261 | 7/1974 | Killinger | 128/272 |
| 3,828,779 | 8/1974 | Ogle | 128/218 N |
| 3,889,673 | 6/1975 | Dovey et al. | 128/215 |
| 3,945,382 | 3/1976 | Ogle | 128/272 |
| 4,059,112 | 11/1977 | Tischlinger | 128/272.3 |
| 4,078,565 | 3/1978 | Genese | 128/218 N |

FOREIGN PATENT DOCUMENTS

| | | | |
|---|---|---|---|
| 948948 | 6/1974 | Canada | 128/215 |
| 1441924 | 3/1969 | Fed. Rep. of Germany | 128/218 R |

*Primary Examiner*—John D. Yasko
*Attorney, Agent, or Firm*—Jones, Tullar & Cooper

[57] ABSTRACT

A sheath for protecting and maintaining sterile a syringe needle and for preventing breakage of the needle during use is disclosed. The sheath is mounted on a syringe of the type used for introducing liquid medication into flexible bags for the administration of intravenous solutions, and serves to guide and protect the needle as it is inserted into the flexible inlet tube of such bags and to hold the needle and syringe in alignment during the injection of medication to prevent breakage of the needle. The syringe housing is formed with a boss, or hub, through which the needle extends, and the sheath is secured to this boss by means of an inwardly turned axial mounting collar. An end wall partially closes the protective sheath and abuts the closed end of the syringe housing to provide a relatively large contact area between these two elements to hold them in alignment. The annular collar frictionally engages the syringe body hub to securely hold the protective sheath in place.

The protective sheath preferably is slightly conical, tapering outwardly from its closed end to an open end which is slightly larger in diameter. The open end of the sheath terminates in an outwardly turned annular flange having a flat surface adapted to engage the outer wall of a container to hold the needle and syringe in the proper angular relationship therewith. A suitable cap or cover is provided for the sheath to enclose the syringe needle until it is to be used.

5 Claims, 3 Drawing Figures

PROTECTIVE SHEATH FOR SYRINGE NEEDLE

BACKGROUND OF THE INVENTION

The present invention relates, in general, to syringes for introducing liquid medication into containers such as intravenous solution bags, and more particularly to an improved protective sheath, or hood, for the needle extending from the syringe body.

Syringes particularly designed for use in injecting liquid medication into containers such as flexible bags, glass bottles, or other sterile containers, wherein the medication is to be mixed with another liquid in the container, are well known. Syringes used with flexible bags, for example, are illustrated in U.S. Pat. Nos. 3,828,779 and 3,945,382, both issued to R. W. Ogle. As described in these and similar patents, such syringes comprise an elongated, generally cylindrical hollow body portion having an open end and a closed end. A boss is formed at the closed end, the boss carrying a needle which extends through the length of the tubular body portion, passing through the boss and forming an exterior cannula portion which is adapted to inject fluid into the container. A sheath is generally provided to surround the cannula portion and is mounted at one end on the boss, with the opposite end being adapted to engage the additive-receiving orifice of, for example, an intravenous (IV) solution bag. The open end of the sheath passes over the orifice and guides the cannula into and through a normally closed plug within the orifice, with the sheath generally being designed to limit the distance the cannula can travel into the orifice to prevent it from piercing the container.

Located within and concentric with the syringe housing is an inner cylindrical wall portion which is adapted to receive a vial or other container for the medication which is to be added to the IV bag. The vial includes a resilient stopper which generally has a thin central portion adapted to be pierced by the upper end of the needle carried by the syringe housing. The stopper may be provided with external threads which engage corresponding threads on the interior of the cylindrical wall portion, with the wall of the vial surrounding the wall portion and extending into the annular space between the wall portion and the syringe housing. When the vial is placed over the end of the wall portion and into the syringe, the syringe needle pierces the stopper so that the medication can flow from the vial through the needle and into the IV bag. By pressing the vial down into the syringe housing, the stopper is forced up into the vial and fluid therein is forced out through the needle.

In order to eject the fluid from the vial into the IV bag, it is often necessary to exert considerable force on the vial and syringe housing. Further, because the orifice into which the medication is injected is flexible, the relationship between the syringe and the IV bag is not constant, and it has been found that as a result the needle guide cover often breaks away from the syringe housing boss, causing breakage of the needle or, in some cases, a piercing of the IV solution bag, thereby contaminating the intravenous solution. Further, because of the relatively unsecure connection between the needle sheath and the syringe housing, the sheath can easily be broken away in handling of the syringe even before it is put into use, thus rendering the syringe useless for its intended purpose.

In the needle cover and guide structure typified by the above-mentioned patents, the outer end of the cover is constructed to provide an exact fit with a specifically shaped container orifice, thereby limiting the usefulness of the syringe to that particular container. Thus, the syringe cannot be used as a general purpose device in combination with a variety of containers without removal of the cover for the needle or cannula, and consequent exposure of the needle to contamination.

SUMMARY OF THE INVENTION

It is, therefore, an object of the present invention to provide an improved needle or cannula sheath for use with syringes which overcomes the problems of breakage and consequent contamination, and which further is adapted for use with a wide variety of container orifices.

It is a further object of the invention to provide a needle or cannula sheath which is designed to provide firm and stable guidance between a container orifice and the cannula portion of a syringe to insure that the needle enters the container correctly and without danger of piercing the sides thereof, and further is limited as to the distance which it can travel into the container orifice for the same purpose.

In accordance with the present invention, there is provided a syringe, needle sheath and cap assembly which overcomes the disadvantages of the prior art devices and which provides a secure and accurate guide for the cannula portion of the syringe needle, protecting it against breakage while in use, or beforehand in the manufacturing, shipping and handling of the syringe. Thus, in accordance with the present invention there is provided a protective hood or sheath which is firmly secured to the syringe housing at one end and which extends outwardly to an open distal end portion which is adapted to recieve IV bag and other container inlet openings of various sizes and shapes. A slight taper in the cover or sheath of the present invention not only facilitates manufacture of the device, but serves to guide the container inlet into the sheath and to insure that the cannula enters the approximate center of the inlet device for injection of the liquid medication. The sheath is of sufficient length that the distal end thereof engages the exterior surface of the container into which the medication is to be injected, preventing the inlet device from entering too far into the sheath and thereby limiting the distance which the needle can travel to prevent the needle from piercing the side walls of the container.

Preferably, the sheath does not extend the full length of the cannula, leaving the end thereof extending beyond the distal end of the sheath to accommodate injection of the medication into containers which do not include the elongated inlet openings mentioned above. For example, some glass bottles in use today have a top inlet, or mouth, which is closed by a thin diaphragm, but which has a diameter greater than that of the interior diameter of the sheath. In such cases, the portion of the cannula extending beyond the sheath is of sufficient length to pierce the diaphragm, whereby the medication can be injected into the container without requiring removal of the sheath.

The connection between the sheath and the syringe housing comprises a radially inwardly extending wall at the end of the sheath which abuts the end of the syringe to which it is to be connected. This radially extending wall is at an angle with the side wall of the sheath which corresponds to the angle of the syringe face which it abuts so that there is an intimate contact therebetween along substantially the entire radial extent of the sheath end wall. The inwardly extending end wall terminates in an annular flange which is coaxial with the sheath and which extends into the sheath to form an annular collar which is adapted to engage a corresponding outwardly extending boss, or hubs, formed on the end of the syringe and adapted to carry the syringe needle. The sheath is secured on the syringe body by positioning the collar around the hub so that it engages the hub, and the end wall of the sheath is welded or otherwise secured to the front wall of the syringe body. This arrangement holds the sheath firmly in place, the abutment between the adjacent front face and end wall providing a strong support against lateral deflection of the sheath and consequent loss or breakage of it or of the needle, which can lead to contamination of the medication.

The distal, or outward, end of the sheath is covered by a suitable cap which cooperates with the sheath to maintain the cannula portion of the needle in a sterile condition until the syringe is ready for use.

Thus, the sheath of the present invention provides a sterile cover for a syringe needle, the sheath being securely connected to the syringe body for greatly improved protection against breakage and consequent contamination of the device, and further provides a configuration which facilitates use of the syringe and permits it to be combined with the entrance openings to a variety of containers.

BRIEF DESCRIPTION OF THE DRAWINGS

The foregoing and additional objects, features and advantages of the present invention will become apparent to those of skill in the art upon a consideration of the following detailed description thereof, taken in conjunction with the accompanying drawings, in which.

DESCRIPTION OF A PREFERRED EMBODIMENT

Figure 1:
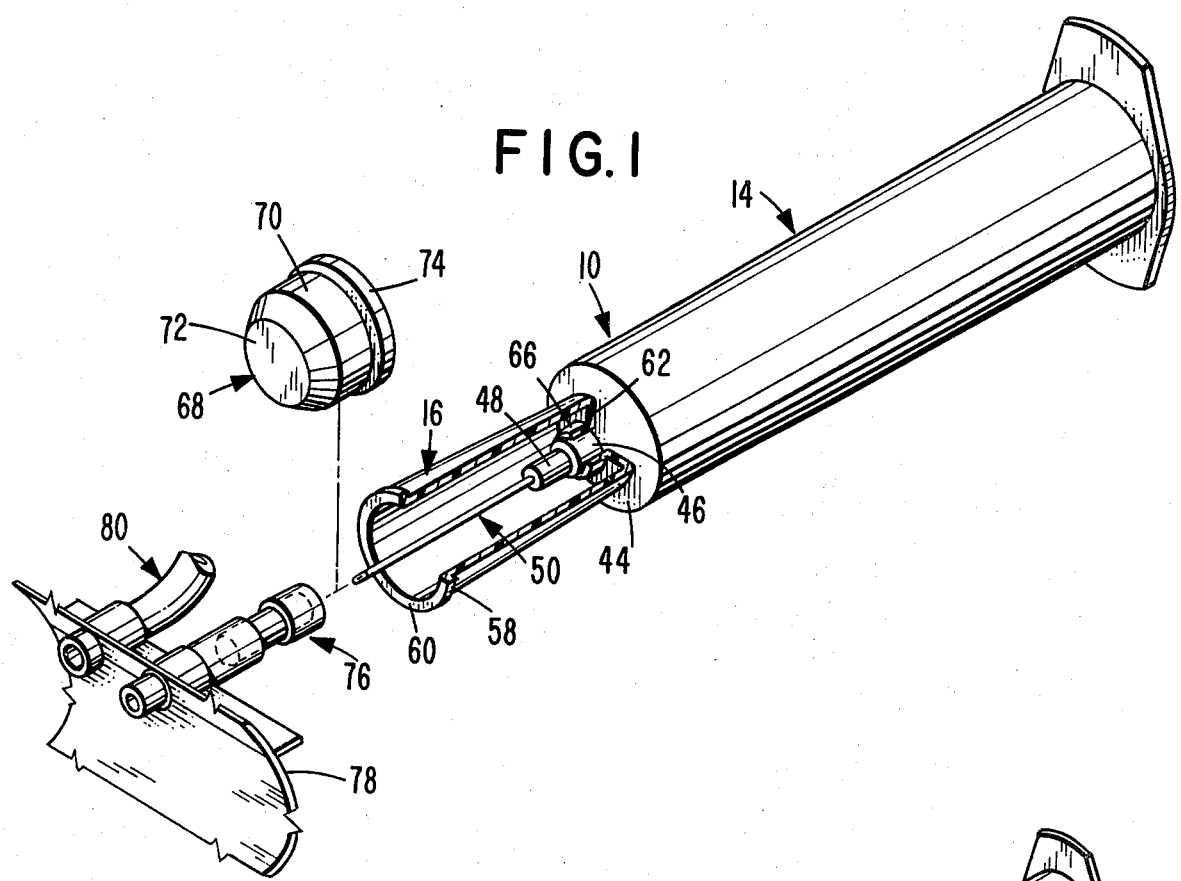
FIG. 1 is a partially exploded, partially sectional view in perspective of a syringe assembly embodying the improved syringe needle cover of the present invention.
Figure 2:
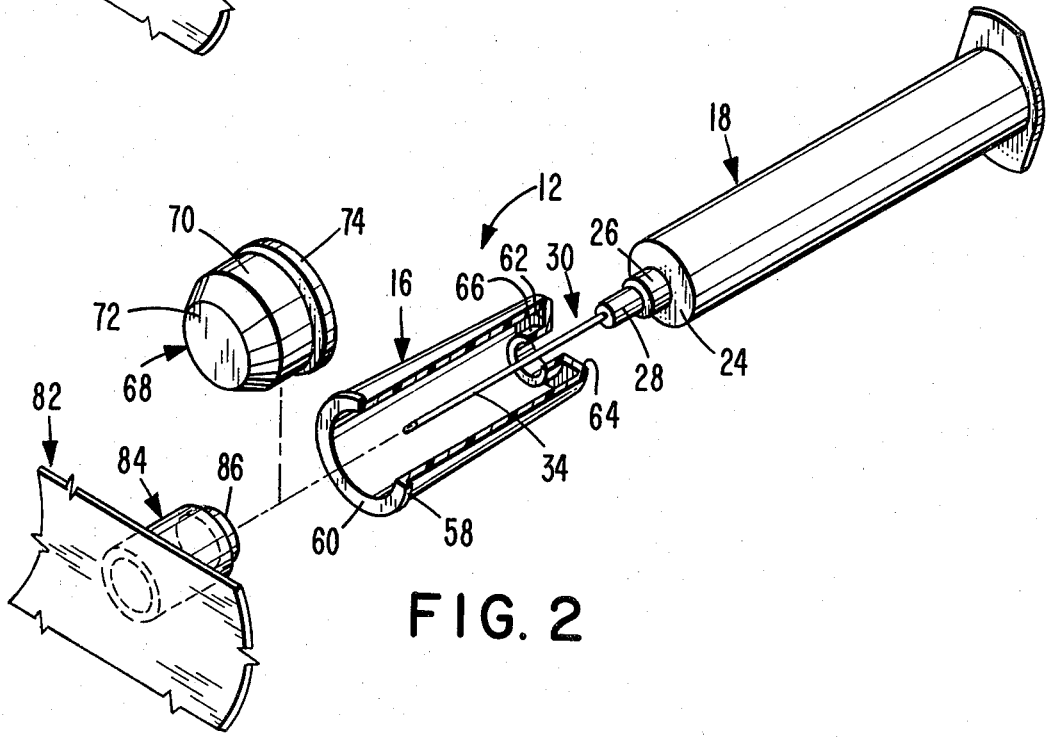
FIG. 2 is an exploded view in partial section of the syringe needle cover of the present invention in combination with a syringe body of smaller capacity.
Figure 3:
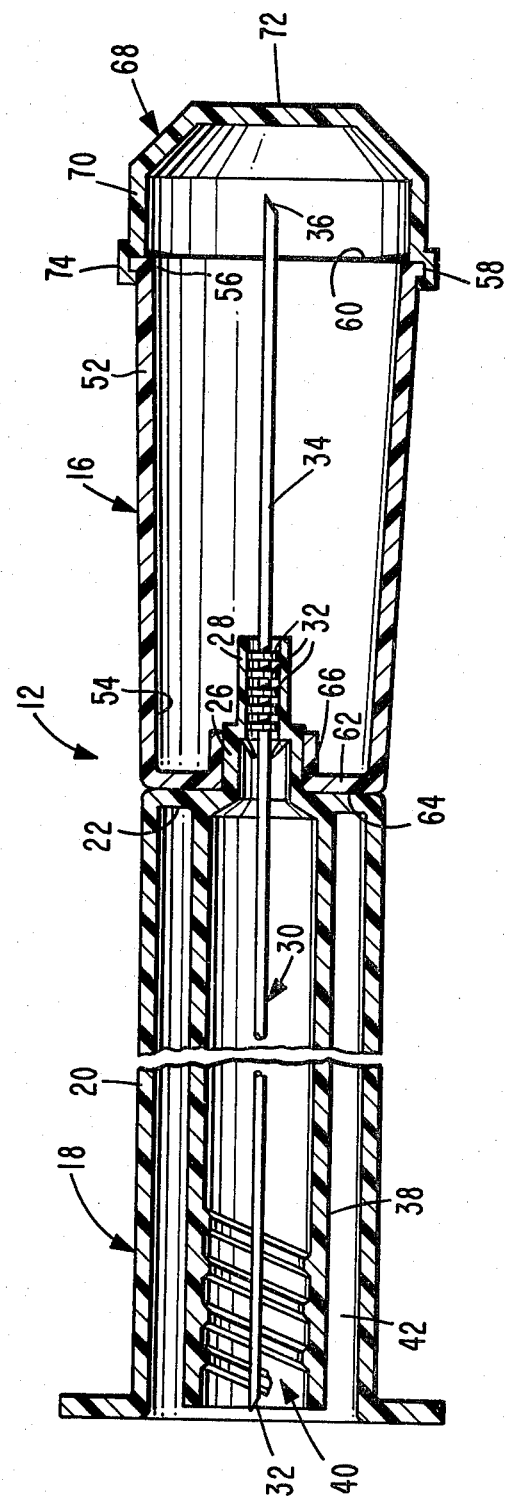
FIG. 3 is a sectional view of the syringe and needle cover assembly of FIG. 2.

Turning now to a more detailed consideration of the invention, there is illustrated in the figures a syringe assembly generally indicated at 10 in FIG. 1 and at 12 in FIGS. 2 and 3. This assembly includes in FIG. 1 a syringe housing 14 to which is secured a syringe needle sheath 16. The syringe housing is illustrated in this figure as being larger in diameter than the sheath 16, the syringe housing representing in this case a device having a capacity of, for example, 50 cc. In FIGS. 2 and 3, the assembly consists of a syringe body 18 to which the needle cover 16 may be secured, but the syringe body is of smaller diameter and may have a capacity of, for example, 10 cc. Thus, it will be recognized that the syringe needle cover of the present invention may be mounted on a variety of syringe housings, the particular syringe depending upon the quantity of medication to be injected or the use to which the device is to be put.

As may be seen more clearly in FIG. 3, the syringe body 18 includes an outer cylindrical wall 20 and a forward end wall 22 which closes one end of the housing and provides on its outer surface a front face 24.

Centrally located in wall 22 is an annular boss, or hub, 26 which is concentric with the housing 18. The hub carries suitable means such as the illustrated mounting post 28 for securing a syringe needle 30 within and coaxial to housing 18. In the illustrated configuration, the mounting post 28 is secured to or is formed as an integral part of the forward end of hub 26 and extends outwardly therefrom, but other configurations may be used. In the illustrated form, the mounting post 28 comprises a hollow cylinder carrying a plurality of mounting discs 32 through which the needle passes and which secure the needle against longitudinal motion in the syringe housing.

As is known in the art, needle 30 extends substantially the full length of housing 18, terminating at its rearward end in a chisel point 32 which is adapted to pierce the stopper in a vial (not shown) of medication or other fluid which is to be injected through the needle. The opposite end of the needle extends out of the mounting post portion of the hub to form the cannula portion 34 of the needle. The distal end of the cannula portion terminates in a chisel point 36 which is adapted to pierce the stopper or other cover for the inlet opening portion of the container into which the medication or other liquid in the vial is to be injected.

The vial of liquid to be injected is secured by means of a threaded stopper (not shown) adapted to engage the upper end of an interior, upstanding, cylindrical wall portion 38 which is concentric to the housing 18 and which is adapted to fit into the vial. The wall portion 38 preferably incorporates suitable threads 40 which receive the corresponding threads on the vial stopper, with the annular space 42 defined between the wall portion 38 and the housing 18 serving to receive the wall of the vial as the medication is ejected through needle 30.

Although not illustrated in FIG. 1, it will be understood that the interior of syringe housing 14 is similar to the syringe housing shown in FIGS. 2 and 3, and thus incorporates a front wall portion 44 which carries a centrally located hub 46 similar to hub 26 of FIGS. 2 and 3, the hub carrying a mounting post 48 which supports a longitudinally extending needle 50.

The needle cover or sheath 16, as illustrated in all three figures, includes a side wall portion 52 which preferably tapers outwardly from its near or small diameter end 54 to its distal or larger diameter end 56, the taper being constant throughout the length of the sheath. The sheath thus forms a truncated cone having a relatively small interior angle so that the wall 52 tapers outward at a relatively small angle. The distal end 56 terminates in an outwardly turned flange 58, the flange having a flat forward surface 60 which preferably lies in a plane perpendicular to the axis of the sheath.

The near, or small diameter, end of the sheath is partially enclosed by an inwardly extending end wall portion 62 which may be formed as a continuation of the side wall portion 52 and which extends substantially radially inwardly to define a rear surface 64. The end, or rear, wall 62 is shown in FIG. 3 as being substantially perpendicular to the axis of sheath 16, but it should be understood that this angle may be varied if desired, the only restriction being that the angle of the rear wall 62 correspond to the angle of the outer surface of the front wall of the syringe housing, i.e., surface 24 of the front wall 22 of syringe 18, so that the walls 22 and 62 will abut each other when the syringe 18 and the sheath 16 are axially aligned and assembled. When the sheath is properly mounted on the syringe housing, the face 24 of the end wall 22 of the syringe body will be in direct abutting contact with the face 64 of the wall 62 of the sheath throughout the corresponding radial extent of the two walls. Thus, if the syringe is of greater diameter than the sheath, the face-to-face contact will be limited to the radial extent of the sheath, while if the syringe is of smaller diameter, the contact will be limited to the radial extent of the syringe housing.

The inwardly turned end wall 62 terminates in an axial flange 66 which defines a circular opening in wall 62 and which defines a support and alignment collar having an inner diameter substantially equal to the outer diameter of the boss 26. The support collar 66 thus serves to align the sheath with the syringe housing 18 when it engages the exterior surface of the boss, so that the sheath will be properly located when it is welded to the face of the syringe body. The angular relationship between the collar 66, wall 62, and wall 52 provides a rigid connecting structure which insures that the sheath will remain in axial alignment with the syringe body to protect the cannula portion 34 of the needle. As shown, flange 66 extends into the interior of the sheath so that it is substantially coextensive with hub 26 to provide a rigid lever arm that protects the sheath against lateral motion with respect to the axis of the syringe and prevents the welded abutting walls from being broken apart.

The distal end of the sheath is adapted to receive a cap 68, the cap including a cylindrical side wall 70 closed at its forward end by means of a forward wall 72 and carrying at its rear, or open, end a shoulder portion 74 which defines an inwardly facing circumferential groove. This groove is adapted to receive the outwardly turned flange 58 formed on the distal end of sheath 16 in a snap fit arrangement whereby the cap 68 may be securely mounted on the sheath to provide a sealed enclosure for the syringe needle. The close fit between the cap 68 and the sheath 16, as well as the close fit between the collar 66 and boss 26 permit maintenance of a sterile atmosphere within the sheath, if desired.

As illustrated in FIGS. 1 and 2, the sheath 16 is adapted to receive a variety of container inlet openings by means of which medication may be injected into the containers. Thus, for example, in FIG. 1, there is illustrated at 76 a conventional flexible orifice of the type used on conventional IV solution bags 78. Orifice 76 is an inlet orifice which contains a suitable plug that is pierced by the cannula portion of needle 50. The end face 60 of the sheath limits the distance which the needle 50 can move into the inlet orifice 76 and when the front edge of the sheath is in engagement with the IV bag 78, it provides stability to the syringe while the medication is being injected. A conventional outlet orifice for the IV bag 78 is indicated at 80.

A different IV bag structure is illustrated in FIG. 2 at 82, this container utilizing a rigid orifice construction as indicated at 84. Inlet orifice 84 is of a larger diameter than the construction illustrated in FIG. 1, and thus would normally require a change in the syringe sheath assembly if medication were to be injected into both containers from the same or a commonly designed syringe. However, with the present invention the same sheath arrangement can be used with both containers, for the sheath 16 will also fit over orifice 84 and guide the needle 30 to pierce the orifice plug 86. Again, the forward wall portion 60 of the sheath engages the container wall 82 to limit the extent of the needle into orifice 84 and to provide stability to the syringe assembly as the fluid is injected. It will be apparent from the foregoing that the sheath 16 is adapted to receive a variety of inlet orifices and to serve as a guide for the syringe needle to insure proper insertion of the needle and stability to the syringe assembly during use.

From the foregoing it may be seen that the present invention provides an improved sheath structure for covering, protecting and guiding syringe needles, and which will prevent and overcome the problems which existed with prior art needle covers. Although the present invention has been disclosed in terms of a preferred embodiment thereof, it will be apparent to those of skill in the art that variations and modifications can be made without departing from the true spirit and scope of the invention as defined in the following claims.

I claim:

1. A syringe assembly including a syringe housing having a front wall substantially closing one end of the housing and hub means one said front wall for receiving and holding a syringe needle, said hub extending forwardly of said front wall and said needle having a cannula portion extending out of said hub and forwardly of said syringe housing, and a protective sheath mounted on said housing coaxially with and spaced radially outwardly from said needle for protecting said cannula portion and extending along at least a portion of the cannula portion, said sheath including:

a substantially cylindrical side wall having a longitudinal axis;

a rear wall located at and substantially closing a first rearward end of said sheath, said rear wall extending generally radially inwardly from said side wall and defining an angle with respect to said axis that corresponds to the angle of said front wall with respect to said syringe needle, whereby when said sheath is mounted on said housing said rear wall of said sheath abuts said front wall of said syringe housing throughout its corresponding radial extent;

annular flange means extending forwardly from said rear wall into said sheath, said flange means being coaxial with said side wall and defining a central aperture, said flange forming a support and alignment collar adapted to receive said hub and cannula portion and to engage said forwardly extending hub to mount said sheath on said housing so that said rear wall abuts said front wall of said housing, said collar being substantially coextensive with said hub within said sheath to provide an axial mounting that resists lateral motion of said sheath with respect to said cannula portion, said sheath being welded to said syringe housing to provide a rigid protective structure; and removable cap means adapted to close the second, forward end of said sheath and enclose said cannula portion.

2. The syringe assembly of claim 1, wherein the side wall of said sheath is tapered to define a truncated cone having a relatively small included angle.

3. The syringe assembly of claim 1, wherein said sheath further includes an outwardly turned annular flange at said second end, said flange having a forward face lying in a plane perpendicular to the axis of said sheath, said flange being adapted to receive said cap means.

4. The syringe assembly of claim 1, wherein said hub means is coaxial with said syringe housing, and said collar is coaxial with said sheath, whereby said sheath is coaxially mounted on said syringe housing.

5. The syringe assembly of claim 1, wherein said sheath further includes an outwardly turned annular flange, and wherein said cap means includes an annular side wall having an internal circumferential groove corresponding to and adapted to receive said outwardly turned annular flange, whereby said cap means is mounted on said sheath.

* * * * *